US011905471B2

(12) United States Patent
Coupard et al.

(10) Patent No.: US 11,905,471 B2
(45) Date of Patent: Feb. 20, 2024

(54) SELECTIVE CATALYST FOR HYDROGENOLYSIS OF ETHYL-AROMATICS BY CONSERVING METHYL-AROMATICS

(71) Applicant: IFP Energies nouvelles, Rueil-Malmaison (FR)

(72) Inventors: Vincent Coupard, Rueil-Malmaison (FR); Anne-Claire Dubreuil, Rueil-Malmaison (FR); Alexandre Jouve, Rueil-Malmaison (FR); Denis Uzio, Rueil-Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 287 days.

(21) Appl. No.: 17/414,882

(22) PCT Filed: Dec. 13, 2019

(86) PCT No.: PCT/EP2019/085011
§ 371 (c)(1),
(2) Date: Jun. 16, 2021

(87) PCT Pub. No.: WO2020/126870
PCT Pub. Date: Jun. 25, 2020

(65) Prior Publication Data
US 2022/0056350 A1 Feb. 24, 2022

(30) Foreign Application Priority Data
Dec. 19, 2018 (FR) ....................... 1873446

(51) Int. Cl.
*C10G 49/04* (2006.01)
*B01J 23/883* (2006.01)
*B01J 35/10* (2006.01)
*B01J 37/02* (2006.01)
*B01J 37/08* (2006.01)

(52) U.S. Cl.
CPC ............ *C10G 49/04* (2013.01); *B01J 23/883* (2013.01); *B01J 35/1009* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 37/0205* (2013.01); *B01J 37/088* (2013.01)

(58) Field of Classification Search
CPC ................ B01J 35/1009; B01J 35/1014; B01J 35/1038; B01J 35/1042; B01J 35/1047; B01J 37/0205; B01J 37/088; C01G 49/04
USPC ......... 502/305, 315; 585/419, 266, 270, 276
See application file for complete search history.

(56) References Cited

U.S. PATENT DOCUMENTS

| | | | | |
|---|---|---|---|---|
| 3,228,858 A | * | 1/1966 | Matyear | C02F 1/06 585/956 |
| 3,692,858 A | * | 9/1972 | Brewer | C10G 47/00 208/89 |
| 3,919,339 A | * | 11/1975 | Ransley | C07C 4/12 585/481 |
| 4,177,219 A | * | 12/1979 | Feinstein | B01J 23/60 208/46 |
| 4,357,263 A | * | 11/1982 | Heck | C10G 45/08 502/313 |
| 5,494,879 A | | 2/1996 | Jin et al. | |
| 5,952,535 A | * | 9/1999 | King | B01J 29/18 585/475 |
| 6,398,950 B1 | * | 6/2002 | Iwamoto | B01J 23/8877 208/143 |
| 6,860,987 B2 | | 3/2005 | Plantenga et al. | |
| 2001/0036902 A1 | * | 11/2001 | Petit-Clair | B01J 37/0211 502/305 |
| 2002/0016258 A1 | | 2/2002 | Wu et al. | |
| 2007/0090023 A1 | * | 4/2007 | Soled | B01J 23/888 502/313 |

FOREIGN PATENT DOCUMENTS

| | | | | |
|---|---|---|---|---|
| CA | 3036380 A1 | * | 4/2018 | ............ B01J 29/068 |
| EP | 0963975 A1 | * | 12/1999 | ............. B01J 23/74 |
| EP | 0963975 A1 | | 12/1999 | |
| FR | 3104463 A1 | * | 6/2021 | ............ B01J 23/883 |
| WO | 9419102 A1 | | 9/1994 | |
| WO | 0041810 A1 | | 7/2000 | |
| WO | 0204117 A1 | | 1/2002 | |

OTHER PUBLICATIONS

English translation of Written Opinion for PCT/EP2019/085011. (Year: 2020).*
International Search Report PCT/EP2019/085011 dated Jan. 24, 2020 (pp. 1-3).
K. J. Jik J. Uchytil M. Kraus: "Hydrodealkylation of alkylbenzenes on a nickel-molybdenum/alumina catalyst", Applied Catalysis, vol. 35, 1987, pp. 289-298, XP002794721, DOI: 10.1016/S0166-9834(00)82867-5.

* cited by examiner

*Primary Examiner* — Patricia L. Hailey
(74) *Attorney, Agent, or Firm* — Ryan R. Pool; MILLEN, WHITE, ZELANO & BRANIGAN, P.C.

(57) ABSTRACT

The present invention relates to a hydrogenolysis process wherein a hydrocarbon-based feedstock comprising aromatic compounds having at least 8 carbon atoms is treated by means of a hydrogen feed and in the presence of a catalyst, in order to convert C2+ alkyl chains of said aromatic compounds into methyl groups and to produce a hydrogenolysis effluent enriched in methyl-substituted aromatic compounds, wherein the catalyst comprises a support, comprising at least one refractory oxide, and an active phase comprising nickel and molybdenum, wherein: the nickel content being between 0.1 and 25% by weight relative to the total weight of the catalyst; the molybdenum content being between 0.1 and 20% by weight relative to the total weight of the catalyst; and the catalyst comprising a molar ratio of molybdenum to nickel of between 0.2 and 0.9. The present invention also relates to said catalyst and to the process for preparing said catalyst.

5 Claims, No Drawings

SELECTIVE CATALYST FOR HYDROGENOLYSIS OF ETHYL-AROMATICS BY CONSERVING METHYL-AROMATICS

TECHNICAL FIELD

The invention pertains to the conversion of aromatics in the context of the production of aromatics for the petrochemical industry (benzene, toluene, para-xylene, ortho-xylene). The aromatic complex is supplied with C6 to C10+ feedstocks, and the aromatic alkyls therein are extracted and then converted into the desired intermediates. The products of interest are aromatics with 0, 1 or 2 methyls, xylenes having the greatest market value. It is thus appropriate to have available methyl groups.

PRIOR ART

A hydrodealkylation reaction is a dealkylation reaction (substitution, in a molecule, of a hydrogen atom for an alkyl radical) wherein the removal of the alkyl group from aromatic-type molecules is carried out in the presence of hydrogen. Specifically, it is a terminal cleavage of the alkyl chain "flush" with the nucleus. The catalysis can be of the acid type, used in particular on alkyl chains with 2 or more carbons but very inefficient for methyls, or of the metal type, when it is desired in particular to convert methyls. The conversion of methyls is used in particular for reducing the cut point of gasolines for which all the molecules must lose carbons, or for the production of benzene for which the reaction is pushed to the maximum in order to keep only the aromatic nucleus.

A hydrogenolysis reaction is a chemical reaction by which a carbon-carbon or carbon-heteroatom covalent bond is broken down or undergoes lysis by the action of hydrogen. A hydrodealkylation reaction can therefore be considered to be a reaction for hydrogenolysis of the carbon-carbon bond between an alkyl and an aromatic nucleus. On the other hand, a hydrogenolysis reaction also concerns the carbon-carbon bonds internal to the alkyl group with 2 or more carbons.

Hydrodealkylation units, mainly used to produce high purity benzene from toluene, are known from the prior art. The McDermott (formerly CB&I) LITOL and DETOL processes are examples of hydrodealkylation which can be either thermal or catalytic. Commercial hydrodealkylation units generally use metal catalysis, which involves a reaction of hydrogenolysis type. The term hydrodealkylation is therefore not exclusive and alkyls with 2 or more carbons also undergo hydrogenolysis therein. Units of this type can be called alkyl aromatic hydrogenolysis units.

The units mentioned above are used either to produce benzene from heavier mono aromatics (toluene, xylenes, etc.), or to reduce the cut point of gasolines. No particular attention is paid to the total amount of methyls available after the conversion unit.

The publication "Hydrogenolysis of ethylbenzene over a supported nickel catalyst derived from nickel hydroaluminate" by C. Hoang-Van, B. L. Villemin and S. J. Teichnern, published in the Journal of Catalysis, volume 105, pages 469-477 (1987), describes the use of a nickel-based catalyst for carrying out the hydrolysis of ethylbenzene to toluene, benzene and paraffins. This article shows that nickel-based catalysts carry out the hydrogenolysis of ethylbenzene with selectivity on the aliphatic carbon. In this document, only nickel-based catalysts are mentioned, and the hydrogenation of the aromatic ring is always observed in parallel with the hydrogenolysis pathway. In addition, the case of a feedstock mixture is not mentioned.

U.S. Pat. No. 4,177,219 describes catalysts for the conversion of ethyl aromatics to methyl aromatics. This patent details a transformation pathway carrying out the conversion of ethyl aromatics to methyl aromatics. It details, in its prior art, catalysts that can be used on the hydrogenolysis of methyl aromatics or more for producing benzene, catalysts based on nickel or on metals that are more noble (ruthenium). Cobalt and chromium alloys are also mentioned. This patent proposes an alloy catalyst based on a group VIII metal promoted by zinc on an alumina of at least 100 $m^2/g$ as the catalyst of choice for the selective conversion of ethyl aromatics to methyl aromatics.

The publication "Hydrodealkylation of alkylbenzenes on a nickel-molybdenum/alumina catalyst" by K. J. Jik, J. Uchytil, and M. Kraus, published in Applied Catalysis, volume 35, pages 289-298 (1987), describes the use of catalysts based on Ni and Mo for the hydrodealkylation of aromatics. The catalyst is a catalyst comprising 3.4% NiO and 17.7% $MoO_3$ on alumina. The hydrogenolysis rate constants were calculated for this catalyst and show that, under the targeted conditions, the catalyst is more active on trimethylbenzenes than on ethylbenzenes. The concept of selectivity between ethyl and methyl group is not explicitly detailed in this publication, the objective being complete hydrodealkylation.

SUMMARY OF THE INVENTION

In the context described above, a first object of the present description is to overcome the problems of the prior art and to carry out a selective hydrogenolysis of ethyl aromatics making it possible in particular to reduce the hydrogenolysis of methyl aromatics, to increase the amounts of methyl groups on the aromatics, to keep a maximum number of aromatic rings, and to limit the side reactions on the products formed.

Continuing its research in the field of hydrogenolysis catalysts, the applicant has now found that it is possible to prepare catalysts that are particularly active, and particularly selective for the hydrogenolysis of ethyl aromatics, the preservation of methyl aromatics, and the limitation of demethylation reactions on the products formed.

According to a first aspect, the abovementioned objects, and also other advantages, are obtained by a hydrogenolysis process wherein a hydrocarbon-based feedstock comprising aromatic compounds having at least 8 carbon atoms is treated by means of an introduction of hydrogen and in the presence of a catalyst, to convert C2+ alkyl chains of said aromatic compounds into methyl groups and to produce a hydrogenolysis effluent enriched in methyl-substituted aromatic compounds, wherein the hydrogenolysis process is carried out with the following operating conditions:
  temperature of between 300° C. and 550° C.;
  pressure of between 0.1 and 3 MPa;
  $H_2$/HC molar ratio of between 1 and 10;
  WWH of between 0.1 and 50 $h^{-1}$, and
  wherein the catalyst comprises a support comprising at least one refractory oxide, and an active phase comprising nickel and molybdenum, wherein:
    the nickel content is between 0.1 and 25% by weight relative to the total weight of the catalyst;
    the molybdenum content is between 0.1 and 20% by weight relative to the total weight of the catalyst; and the catalyst comprises a molar ratio of molybdenum to nickel (Mo/Ni) of between 0.2 and 0.9.

According to one or more embodiments,
the nickel content is between 0.2 and 15% by weight relative to the total weight of the catalyst;
the molybdenum content is between 0.2 and 18% by weight relative to the total weight of the catalyst; and
the catalyst comprises a molar ratio of molybdenum to nickel of between 0.5 and 0.9.

According to one or more embodiments,
the nickel content is between 0.5 and 10% by weight relative to the total weight of the catalyst;
the molybdenum content is between 0.4 and 15% by weight relative to the total weight of the catalyst; and
the catalyst comprises a molar ratio of molybdenum to nickel of between 0.4 and 0.9.

According to one or more embodiments, the specific surface area (BET) of the refractory oxide is between 1 $m^2/g$ and 250 $m^2/g$.

According to one or more embodiments, the pore volume (Vp) of the refractory oxide is between 0.1 and 2 $cm^3/g$.

According to a second aspect, the abovementioned objects, and also other advantages, are obtained by a process for the production of xylenes integrating the hydrogenolysis process according to the first aspect, in order to enrich streams in aromatics comprising methyl groups, all or a portion of which are sent to an aromatic complex in order to produce xylenes.

It is well known that an aromatic complex is a unit for the treatment (e.g. separation, purification, transformation (e.g. isomerization, transalkylation)) of aromatics.

According to one or more embodiments, at least one hydrogenolysis process is integrated into an aromatic complex according to at least one of the following configurations:
the at least one hydrogenolysis process is used to pretreat a hydrocarbon-based feedstock upstream of the aromatic complex;
the at least one hydrogenolysis process is used to treat at least one cut internal to the aromatic complex.

According to a third aspect, the abovementioned objects, and also other advantages, are obtained by a hydrogenolysis catalyst, for the hydrogenolysis of a hydrocarbon-based feedstock comprising aromatic compounds having at least 8 carbon atoms, the catalyst comprising a support, comprising at least one refractory oxide, and an active phase comprising nickel and molybdenum, wherein:
the nickel content being between 0.1 and 25% by weight relative to the total weight of the catalyst;
the molybdenum content being between 0.1 and 20% by weight relative to the total weight of the catalyst; and
the catalyst comprises a molar ratio of molybdenum to nickel of between 0.2 and 0.9.

According to one or more embodiments,
the nickel content is between 0.5 and 10% by weight relative to the total weight of the catalyst;
the molybdenum content is between 0.4 and 15% by weight relative to the total weight of the catalyst; and
the catalyst comprises a molar ratio of molybdenum to nickel of between 0.5 and 0.9.

According to one or more embodiments, the specific surface area (BET) of the refractory oxide is between 1 $m^2/g$ and 250 $m^2/g$; and/or the pore volume (Vp) of the refractory oxide is between 0.1 and 2 $cm^3/g$.

According to a fourth aspect, the abovementioned objects, and also other advantages, are obtained by a process for preparing a hydrogenolysis catalyst,
the hydrogenolysis catalyst comprising a support comprising at least one refractory oxide, and an active phase comprising nickel and molybdenum, wherein:
the nickel content being between 0.1 and 25% by weight relative to the total weight of the catalyst;
the molybdenum content being between 0.1 and 20% by weight relative to the total weight of the catalyst; and
the catalyst comprising a molar ratio of molybdenum to nickel of between 0.2 and 0.9,
the preparation process comprising the following steps:
a) a step of bringing the support into contact with at least one solution containing at least one nickel precursor is carried out;
b) a step of bringing the support into contact with at least one solution containing at least one molybdenum precursor is carried out,
step b) being carried out after step a) or steps a) and b) being carried out together; preferably, step a) is carried out before step b);
c) at least one step of drying the catalyst precursor obtained at the end of step a) and/or of step b) is carried out at a temperature of less than 250° C.;
d) a step of reducing the catalyst precursor obtained at the end of step c) is carried out by bringing said catalyst precursor into contact with a reducing gas at a temperature of between 350 and 450° C.

According to one or more embodiments, the preparation process comprises the following steps:
a) a step of bringing the support into contact with at least one solution containing at least one nickel precursor is carried out;
ca) at least one step of drying the catalyst precursor obtained at the end of step a) is carried out at a temperature of less than 250° C.;
b) a step of bringing the catalyst precursor obtained at the end of step ca) into contact with at least one solution containing at least one molybdenum precursor is carried out;
cb) at least one step of drying the catalyst precursor obtained at the end of step b) is carried out at a temperature of less than 250° C.;
d) a step of reducing the catalyst precursor obtained at the end of step cb) is carried out by bringing said catalyst precursor into contact with a reducing gas at a temperature of between 350 and 450° C.

According to one or more embodiments, the preparation process comprises the following steps:
ab) a step of bringing the support into contact with at least one solution containing at least one nickel precursor and at least one molybdenum precursor is carried out;
c) at least one step of drying the catalyst precursor obtained at the end of step ab) is carried out at a temperature of less than 250° C.;
d) a step of reducing the catalyst precursor obtained at the end of step c) is carried out by bringing said catalyst precursor into contact with a reducing gas at a temperature of between 350 and 450° C.

According to one or more embodiments, the nickel precursor is nickel carbonate.

According to one or more embodiments, the catalyst precursor undergoes an additional heat treatment step at a temperature of between 250 and 1000° C., directly after a drying step.

Embodiments according to the abovementioned aspects and also other characteristics and advantages of the processes and catalysts according to the abovementioned aspects will emerge on reading the description which follows, given by way of illustration only and not as limitation.

DESCRIPTION OF THE EMBODIMENTS

In the petrochemical industry, para-xylene is one of the intermediates with the highest market value. The production thereof requires methyl-substituted monoaromatics; it is mainly produced by disproportionation of toluene, isomerization of xylenes or trans-alkylation of toluene with tri- or tetramethylbenzenes. To maximize the production of para-xylene, it is useful to maximize the amount of methyl group available per aromatic nucleus.

With this in mind, methyl-substituted monoaromatics, preferably monoaromatics substituted only with methyls, can be directly exploited, which is not the case with monoaromatics containing little or no methyl (example: ethylbenzene, propylbenzene, methylethylbenzene). It is therefore preferable to convert these monoaromatics into aromatics (e.g only) substituted with methyl. In this context, a hydrogenolysis unit capable of increasing the amount of methyl groups on the aromatic rings, in particular to increase the production of para-xylene, has been developed. The objective of the hydrogenolysis unit according to the present invention is to produce methyl groups instead of and in place of alkyl groups having more than two carbon atoms.

Specifically, the object of the invention is to improve the performance levels of the hydrogenolysis unit. It has been observed that NiMo-type bimetallic catalysts can be selective for the hydrogenolysis of ethyl aromatics, the preservation of methyl aromatics, and the limitation of demethylation reactions on the products formed.

In the subsequent text, the groups of chemical elements are given, by default, according to the CAS classification (CRC Handbook of Chemistry and Physics, published by CRC Press, Editor in Chief D. R. Lide, 81st edition, 2000-2001). For example, group VIII according to the CAS classification corresponds to the metals of columns 8, 9 and 10 according to the new IUPAC classification.

The term "specific surface area" of the catalyst or of the support used for the preparation of the catalyst according to the invention is understood to mean the BET specific surface area determined by nitrogen adsorption in accordance with Standard ASTM D 3663-78 drawn up from the Brunauer-Emmett-Teller method described in the journal "The Journal of American Society", 60, 309 (1938).

The term "pore volume" of the catalyst or of the support used for the preparation of the catalyst according to the invention is intended to mean the volume measured by intrusion with a mercury porosimeter according to Standard ASTM D4284-83 at a maximum pressure of 4000 bar (400 MPa), using a surface tension of 484 dyne/cm and a contact angle of 140°. The wetting angle was taken equal to 140° following the recommendations of the work "Techniques de l'ingénieur, traité analyse et caractérisation" [Techniques of the Engineer, Analysis and Characterization Treatise], pages 1050-1055, written by Jean Charpin and Bernard Rasneur.

In order to obtain better accuracy, the value of the pore volume corresponds to the value of the pore volume measured by intrusion with a mercury porosimeter measured on the sample minus the value of the pore volume measured by intrusion with a mercury porosimeter measured on the same sample for a pressure corresponding to 30 psi (approximately 0.2 MPa).

A—Catalyst

The catalyst according to the invention comprises a NiMo-type bimetallic catalyst and comprises a support comprising at least one refractory oxide, and an active phase. Said active phase is based on nickel for in particular promoting terminal hydrogenolysis of the alkyl chains, and based on molybdenum, a selectivating metal, for limiting the positions of adsorption of aromatics on the metal particles.

The nickel content is between 0.1 and 25% by weight of said element relative to the total weight of the catalyst, preferably between 0.2 and 15%, and even more preferentially between 0.5 and 10% by weight relative to the total weight of the catalyst.

The molybdenum content is between 0.1 and 20% by weight of said element relative to the total weight of the catalyst, preferably between 0.2 and 18% by weight, preferably between 0.4 and 15% by weight relative to the total weight of the catalyst.

The catalyst comprises a molar ratio of molybdenum to nickel (Mo/Ni) of between 0.2 and 0.9 (mol/mol), preferably between 0.4 and 0.9, and even more preferentially between 0.5 and 0.9.

According to one or more embodiments, the refractory oxide may or may not be crystalline, and may or may not have a structured porosity. According to one or more embodiments, the refractory oxide is selected from the oxides of metals from groups 2, 3, 4, 13 and 14 of the IUPAC new periodic table of elements, such as, for example, the oxides of magnesium, aluminum, silicon, titanium, zirconium, thorium, taken alone or as a mixture with each other, or as a mixture with other oxides of metals of the periodic table. According to one or more embodiments, the refractory oxide is inorganic. According to one or more embodiments, the refractory oxide is essentially neutral in terms of acidity-basicity. According to one or more embodiments, the refractory oxide is chosen from silicas of low surface area (i.e. BET <250 $m^2/g$; e.g. with less than 100 ppm by weight of Al), titanium oxides, aluminas (e.g. with less than 100 ppm by weight of Si), clays and charcoals. According to one or more embodiments, the refractory oxide is heat pretreated, optionally in the presence of water. According to one or more embodiments, the porous support is chosen from the group consisting of silica and alumina. According to one or more embodiments, the support is alumina.

According to one or more embodiments, the refractory oxide is hydrothermally pretreated, for example to adjust its surface area (in the sense of the BET surface) downwards and its pore distributions upwards.

According to one or more embodiments, the specific surface area (BET) of the refractory oxide is generally greater than 1 $m^2/g$ and less than 250 $m^2/g$, for example between 2 and 200 $m^2/g$, preferably between 5 and 100 $m^2/g$, preferentially less than 100 $m^2/g$, and even more preferentially between 20 and 90 $m^2/g$, such as approximately 80 $m^2/g$.

According to one or more embodiments, the pore volume (Vp) of the refractory oxide is between 0.1 and 2 $cm^3/g$, preferably between 0.3 and 1.5 $cm^3/g$, and even more preferentially between 0.9 and 1.1 $cm^3/g$, such as approximately 1.0 $cm^3/g$.

The refractory oxide can also include impurities (e.g. Ca, K, P, Mg, Fe, Si, Ti, W). According to one or more embodiments, the refractory oxide comprises less than 500 ppm by weight of impurities, preferably less than 200 ppm by weight of impurities, and even more preferentially less than 100 ppm by weight of impurities relative to the total weight of the refractory oxide.

The catalyst can also comprise at least one basic compound in order to limit reactions of an acidic nature (dealkylation of isopropylbenzene for example). According to one or more embodiments, the at least one basic compound is chosen from the group consisting of Na, K, Li and Ca. According to one or more embodiments, the content of basic compound is between 1 and 3% by weight, preferably between 1 and 2% by weight, of said basic compound relative to the total weight of the catalyst.

Said catalyst is generally presented in all the forms known to those skilled in the art, for example in the form of beads (generally having a diameter of between 1 and 8 mm), of extrudates, of blocks or of hollow cylinders. According to one or more embodiments, the catalyst consists of extrudates with a mean diameter generally of between 0.5 and 10 mm, preferably between 0.8 and 3.2 mm and very preferably between 1.0 and 2.5 mm and optionally with a mean length of between 0.5 and 20 mm. The term "mean diameter" of the extrudates is intended to mean the mean diameter of the circle circumscribed in the cross section of these extrudates. The catalyst can advantageously be presented in the form of cylindrical, multilobal, trilobal or quadrilobal extrudates. Preferably, its shape will be trilobal or quadrilobal. The shape of the lobes could be adjusted according to all the methods known from the prior art.

B—Process for Preparing the Catalyst

The process for preparing the bimetallic catalyst comprises the following steps:
- a) a step of bringing the support into contact with at least one solution containing at least one nickel precursor is carried out;
- b) a step of bringing the support into contact with at least one solution containing at least one molybdenum precursor is carried out,
- step b) being carried out after step a) or steps a) and b) being carried out together, preferably, step a) is carried out before step b);
- c) at least one step of drying the catalyst precursor obtained at the end of step a) and/or of step b) is carried out at a temperature of less than 250° C.;
- d) a step of reducing the catalyst precursor obtained at the end of step c) is carried out by bringing said catalyst precursor into contact with a reducing gas at a temperature of between 350 and 450° C.

According to one or more embodiments, the process for preparing the bimetallic catalyst comprises the following steps:
- a) a step of bringing the support into contact with at least one solution containing at least one nickel precursor is carried out;
- ca) at least one step of drying the catalyst precursor obtained at the end of step a) is carried out at a temperature of less than 250° C.;
- b) a step of bringing the catalyst precursor obtained at the end of step ca) into contact with at least one solution containing at least one molybdenum precursor is carried out;
- cb) at least one step of drying the catalyst precursor obtained at the end of step b) is carried out at a temperature of less than 250° C.;
- d) a step of reducing the catalyst precursor obtained at the end of step cb) is carried out by bringing said catalyst precursor into contact with a reducing gas at a temperature of between 350 and 450° C.

According to one or more embodiments, the process for preparing the bimetallic catalyst comprises the following steps:
- ab) a step of bringing the support into contact with at least one solution containing at least one nickel precursor and at least one molybdenum precursor is carried out;
- c) at least one step of drying the catalyst precursor obtained at the end of step ab) is carried out at a temperature of less than 250° C.;
- d) a step of reducing the catalyst precursor obtained at the end of step c) is carried out by bringing said catalyst precursor into contact with a reducing gas at a temperature of between 350 and 450° C.

The steps of the process for preparing the catalyst are explained in detail below.

Step a) Bringing into Contact the Nickel Precursor

The deposition of nickel on said support, in accordance with the implementation of step a), can be carried out by impregnation, dry or in excess, or even by deposition-precipitation, according to methods well known to those skilled in the art.

Said step a) is preferentially carried out by impregnation of the support, for example by bringing said support into contact with at least one aqueous solution and/or organic solution (for example with at least one organic solvent, such as methanol and/or ethanol and/or phenol and/or acetone and/or toluene and/or dimethyl sulfoxide). Preferably, the organic solvent can be vaporized in the heat treatment steps. Preferably, the solution contains at least one nickel precursor at least partially in the dissolved state. According to one or more embodiments, said support is brought into contact with at least one colloidal solution of at least one nickel precursor, in oxidized form (nickel oxide, oxy(hydroxide) or hydroxide nanoparticles) or in reduced form (metal nanoparticles of nickel in the reduced state).

Preferably, the solution is aqueous. According to one or more embodiments, the pH of the aqueous solution is modified by adding an acid or a base, preferably by adding a base. According to one or more embodiments, the pH of the aqueous solution is greater than 11, preferably between 11 and 13, even more preferentially between 11 and 12, such as approximately 11.5. According to one or more embodiments, the aqueous solution contains aqueous ammonia or $NH_4^+$ ammonium ions. For example, the aqueous solution can be an aqueous ammonia solution, optionally with a buffer solution to regulate a pH during the impregnation phase which is constant (e.g. use of an ammonium carbonate salt). According to one or more embodiments, the pH of the aqueous solution is adjusted by means of a mixture of ammonia ($NH_3$) and ammonium carbonate ($(NH_4)_2CO_3$.

Preferably, said step a) is carried out by dry impregnation, which comprises bringing the catalyst support into contact with a solution containing at least one nickel precursor, of which the volume of the solution is between 0.75 and 1.25 times, preferably between 0.8 and 1.2 times, preferably between 0.9 and 1.1 times, even more preferentially between 0.95 and 1.05 times, the pore volume of the support to be impregnated.

According to one or more embodiments, when the nickel precursor is introduced in aqueous solution, it is in the form of carbonate, acetate, chloride, hydroxide, hydroxycarbonate, oxalate, sulfate, formate, nitrate, complexes formed by a polyacid or an acid-alcohol and its salts, complexes formed with acetylacetonates, tetrammine or hexammine complexes, or even any other inorganic derivative soluble in aqueous solution.

Nickel carbonate, nickel hydroxide, nickel chloride, nickel hydroxycarbonate and/or nickel nitrate is preferably advantageously used as nickel precursor. Very preferably, the nickel precursor is nickel carbonate. Even more preferably, the nickel precursor is ammoniacal nickel carbonate (e.g. nickel carbonate+ammonia). A particular effect of nickel carbonate, and in particular of ammoniacal nickel carbonate, used as a precursor, is that it allows better low-temperature decomposition, promoting dispersion of the active phase.

Step b) Bringing into Contact the Molybdenum Precursor

The deposition of molybdenum on said support, in accordance with the implementation of step b), can be carried out by dry impregnation or excess impregnation, or also by deposition-precipitation, according to methods well known to those skilled in the art.

Said step b) is preferentially carried out by impregnation of the support, for example by bringing said support into contact with at least one aqueous solution and/or organic solution (for example with a solution comprising methanol and/or ethanol and/or phenol and/or acetone and/or toluene and/or dimethyl sulfoxide). Preferably, the organic solvent can be vaporized in the heat treatment steps. Preferably, the solution contains at least one molybdenum precursor at least partially in the dissolved state.

Preferably, the solution is aqueous. According to one or more embodiments, the pH of the aqueous solution is modified by adding an acid or a base, preferably by adding a base.

According to one or more embodiments, the pH of the aqueous solution is greater than 11, preferably between 11 and 13, even more preferentially between 11 and 12, such as approximately 11.5. According to one or more embodiments, the aqueous solution contains aqueous ammonia or $NH_4^+$ ammonium ions. For example, the aqueous solution can be an aqueous ammonia solution, optionally with a buffer solution to regulate a pH during the impregnation phase which is constant (e.g. use of an ammonium carbonate salt). According to one or more embodiments, the pH of the aqueous solution is adjusted by means of a mixture of ammonia ($NH_3$) and ammonium carbonate ($NH_4)_2CO_3$.

Preferably, said step b) is carried out by dry impregnation, which comprises bringing the catalyst support into contact with a solution containing at least one molybdenum precursor, of which the volume of the solution is between 0.75 and 1.25 times, preferably between 0.8 and 1.2 times, preferably between 0.9 and 1.1 times, even more preferentially between 0.95 and 1.05 times, the pore volume of the support to be impregnated.

When the molybdenum precursor is introduced in aqueous solution, a molybdenum precursor in mineral or organic form is preferably used.

In mineral form, the molybdenum precursor can be chosen from ammonium heptamolybdate, or any other precursor obtained by dissolving $MoO_3$ in a mineral and organic acid or any other heteropolyanion containing molybdenum, or phosphomolybdic precursors (e.g. $H_3PMo_{12}O_{40}$). In organic form, the molybdenum precursor can be chosen from organometallic complexes obtained by reaction between a molybdenum oxide or sulfide and a fatty acid. Preferably, the molybdenum precursor comprises ammonium heptamolybdate.

Steps a) and b) can be performed together. Preferably, the impregnation of the nickel precursor is carried out before the impregnation of the molybdenum precursor, so as to avoid the formation of catalytic sites where the nickel atoms are too exposed, which is less desirable in the context of the present invention because that can lead to poorer activity and/or selectivity.

Step c) Drying the Impregnated Support

Step c) of drying the catalyst precursor obtained at the end of step a) and of step b) is carried out at a temperature of less than 250° C., preferably between 15 and 240° C., more preferentially between 30 and 220° C., even more preferentially between 50 and 200° C., and even more preferentially between 70 and 180° C. (e.g. at approximately 150° C.), for a period typically of between 5 minutes and 24 hours (e.g. for approximately 30 minutes). Longer periods of time are not ruled out, but do not necessarily afford any improvement. The drying step can be carried out by any technique known to those skilled in the art. It is advantageously carried out under an inert atmosphere or under an oxygen-containing atmosphere or under a mixture of inert gas and oxygen. It is advantageously carried out at atmospheric pressure or at reduced pressure. Preferably, this step is carried out at atmospheric pressure and in the presence of air and/or of nitrogen.

According to one or more embodiments, the drying step comprises a first period of maturation (gentle drying), then a second period of evaporation (strong drying) carried out between 30 and 220° C. According to one or more embodiments, the maturation step is carried out at a temperature of less than 30° C. (e.g. at ambient temperature), for a period typically of between 5 minutes and 24 hours (e.g. overnight).

Heat Treatment of the Dried Catalyst (Optional Step)

After a drying step (for example: between step c) and step d); between step ca) and step b) and/or between step cb) and step d)), the dried catalyst precursor can undergo an additional heat treatment step at a temperature of between 250 and 1000° C. and preferably between 250 and 750° C., preferentially between 250 and 500° C. (e.g. at a temperature of approximately 280° C.), for a period typically of between 5 minutes and 10 hours (e.g. for approximately 45 minutes), under an inert atmosphere or under an oxygen-containing atmosphere, optionally in the presence of water. Longer treatment times are not ruled out, but do not necessarily afford an improvement.

The term "heat treatment" is intended to mean temperature treatment respectively without the presence or in the presence of water. In the latter case, contact with the steam can take place at atmospheric pressure or under autogenous pressure. Several combined cycles without the presence or with the presence of water can be performed.

According to one or more embodiments, the process for preparing the bimetallic catalyst comprises a heat treatment step after each drying step c).

According to one or more embodiments, the heat treatment is calcination (heat treatment in the presence of oxygen), optionally in the presence of water.

After this or these treatment(s), the catalyst precursor comprises nickel in oxide form, that is to say in NiO form and also in the form of mixed oxide NiOMo allowing the creation of alloys after the reduction step.

Step d) Reduction with a Reducing Gas

Prior to the use of the catalyst in the catalytic reactor and the implementation of a hydrogenation process, a reducing treatment step d) is carried out in the presence of a reducing gas so as to obtain a catalyst comprising nickel at least partially in the metallic form. This step can be carried out ex situ or in situ. This treatment makes it possible to activate said catalyst and to form metal particles, in particular of nickel in the zero-valent state. The in situ implementation (that is to say after charging the catalyst to a hydrogenolysis reactor) of the treatment to reduce the catalyst makes it possible to dispense with an additional and optional step of passivation of the catalyst with an oxygen-containing or sulfur-containing compound or with $CO_2$, which may be necessary when the catalyst is prepared by carrying out an ex situ reducing treatment (that is to say outside the hydrogenolysis reactor). In fact, when the reducing treatment is carried out ex situ, it may be necessary to carry out a passivation step in order to preserve the metallic phase of the catalyst in the presence of air (during operations of transport and charging of the catalyst to the hydrogenation reactor), then to carry out a new additional step of reducing the catalyst.

The reducing gas is preferably hydrogen. The hydrogen can be used pure or as a mixture (for example a hydrogen/nitrogen, hydrogen/argon or hydrogen/methane mixture). In the case where the hydrogen is used as a mixture, all proportions can be envisaged.

According to one or more embodiments, said reducing treatment is carried out at a temperature of between 350 and 450° C., preferably between 370 and 430° C., even more preferably between 390 and 410° C. (e.g. at a temperature of approximately 400° C.). According to one or more embodiments, the duration of the reducing treatment is between 5 minutes and 48 hours, preferably between 30 minutes and 36 hours, more preferentially between 1 and 24 hours, and even more preferentially between 2 and 20 hours (e.g. a duration of approximately 16 h).

According to one or more embodiments, the rise in temperature up to the desired reduction temperature is slow, for example set between 0.1 and 10° C./min, preferably between 0.3 and 7° C./min.

Step e) Passivation (Optional)

The catalyst prepared according to the process according to the invention can optionally undergo a step of passivation with an oxygen-containing or sulfur-containing compound or with $CO_2$, which makes it possible to improve the selectivity of the catalysts, to avoid thermal runaway during the start-up of new catalysts and to reduce the formation of coke and/or of organic deposits on the catalyst. Such a passivation step is for example useful following the reduction step when the latter is carried out ex situ.

C—Hydrogenolysis Process

A subject of the present invention is also a hydrogenolysis process, using a catalyst according to the invention or a catalyst prepared by the preparation process according to the invention, for treating a hydrocarbon-based feedstock rich in aromatic compounds having at least 8 carbon atoms and converting one or more alkyl group(s) with at least two carbon atoms (ethyl, propyl, butyl, isopropyl, etc., groups) attached to a benzene ring, into one or more methyl group(s), i.e. groups formed from a single $CH_3$ group.

The hydrogenolysis process according to the invention makes it possible to treat the hydrocarbon-based feedstock by means of a supply of hydrogen, and in the presence of the catalyst according to the invention, in order to convert C2+ alkyl chains of the aromatic compounds into methyl groups; and to produce a hydrogenolysis effluent enriched in methyl-substituted aromatic compounds with respect to the hydrocarbon-based feedstock. It is a question of treating the hydrocarbon-based feedstock by converting one or more alkyl group(s) with at least two carbon atoms (ethyl, propyl, butyl, isopropyl, etc., groups) attached to a benzene ring into one or more methyl group(s), i.e., group(s) formed of a single $CH_3$ group.

The hydrogenolysis reaction is carried out with the following operating conditions:

temperature of between 300° C. and 550° C., preferably of between 350° C. and 500° C., preferentially of between 370 and 450° C., even more preferably of between 370 and 430° C. (e.g. between 380 and 410° C.); and/or pressure of between 0.1 and 3 MPa, preferably of between 0.2 and 2 MPa, and more preferentially of between 0.2 and 1 MPa;

$H_2$/HC (hydrocarbon) molar ratio of between 1 and 10, and preferentially of between 1.5 and 6; and/or WWH of between 0.1 and 50 $h^{-1}$, preferentially of between 0.5 and 30 $h^{-1}$, and more preferentially of between 1 and 20 $h^{-1}$ (e.g. between 1 and 7 $h^{-1}$).

The term "WWH" corresponds to the hourly weight of hydrocarbon-based feedstock injected, based on the weight of catalyst charged.

According to one or more embodiments, the hydrogenolysis process is carried out in a hydrogenolysis reactor of the fixed bed or moving bed type. A moving bed may be defined as being a gravity flow bed, such as those encountered in the catalytic reforming of gasolines.

According to one or more embodiments, the process comprises treating the hydrogenolysis effluent by means of a separation unit to produce a plurality of liquid effluent cuts.

According to one or more embodiments, the hydrocarbon-based feedstock is mixed with the hydrogen supply in the hydrogenolysis reactor and/or (e.g. directly) upstream of the hydrogenolysis reactor to form a feedstock mixture.

According to one or more embodiments, the hydrogenolysis process also comprises heating the hydrocarbon-based feedstock or the feedstock mixture in a heating unit (e.g. directly) upstream of the hydrogenolysis reactor. According to one or more embodiments, the heating unit is suitable for use under the following operating conditions: inlet temperature of between 25° C. and 400° C.; and/or outlet temperature of between 300° C. and 550° C. The heating effluent from the heating unit is sent (e.g. directly) to the hydrogenolysis reactor.

According to one or more embodiments, the hydrogenolysis effluent is sent (e.g. directly) to a cooling unit (e.g. heat exchanger) to form a cooled hydrogenolysis effluent. The cooling unit may be preceded by equipment for recovering heat from the effluent used to preheat the hydrocarbon-based feedstock or the feedstock mixture (e.g. upstream of the heating unit). According to one or more embodiments, the cooling unit is suitable for use under the following operating conditions: inlet temperature of between 100° C. and 550° C.; and/or outlet temperature of between 25° C. and 400° C.

According to one or more embodiments, the cooled hydrogenolysis effluent is sent (e.g. directly) to a cooled effluent separation unit to produce a gaseous effluent comprising hydrogen and a liquid effluent.

According to one or more embodiments, the gaseous effluent is sent to a recycling unit suitable for: compressing and/or purifying the gaseous effluent; optionally extracting a purge gas (e.g. methane) from the gaseous effluent; and/or mixing the gaseous effluent with the hydrogen supply to form a mixture of hydrogen sent to the hydrogenolysis reactor and/or (e.g. directly) mixed with the hydrocarbon-based feedstock to form the depleted effluent mixture.

According to one or more embodiments, the liquid effluent is sent to the separation unit to produce the plurality of liquid effluent cuts.

The Feedstock

According to one or more embodiments, the hydrocarbon-based feedstock comprises at least 90% by weight, preferably at least 95% by weight, more preferentially at least 98% by weight (e.g. at least 99% by weight), of aromatic compounds (e.g. aromatics comprising at least 8 carbon atoms, such as aromatics comprising from 8 to 10 carbon atoms) relative to the total weight of the feedstock.

According to one or more embodiments, the aromatic compounds of the hydrocarbon-based feedstock comprise at least 50% by weight, preferably at least 70% by weight, more preferentially at least 90% by weight (e.g. at least 95% by weight), of aromatic compounds comprising at least 9 carbon atoms, relative to the total weight of the aromatic compounds of the hydrocarbon-based feedstock.

According to one or more embodiments, the hydrocarbon-based feedstock comprises at least 90% by weight, preferably at least 95% by weight, more preferentially at least 98% by weight (e.g. at least 99% by weight), of aromatic compounds comprising 9 carbon atoms, relative to the total weight of the feedstock.

According to one or more embodiments, the hydrocarbon-based feedstock comprises at least 90% by weight of aromatic molecules having between 8 and 10 carbon atoms relative to the total weight of the hydrocarbon-based feedstock. According to one or more embodiments, the hydrocarbon-based feedstock comprises at least one internal stream of an aromatic complex for the production of para-xylene and/or the hydrogenolysis effluent is a feedstock sent to an aromatic complex for the production of para-xylene.

According to one or more embodiments, the hydrocarbon-based feedstock comprises at least 90% by weight of aromatic molecules having 8 carbon atoms relative to the total weight of said feedstock. According to one or more embodiments, the hydrocarbon-based feedstock comprises a para-xylene extraction raffinate. According to one or more embodiments, the para-xylene extraction raffinate comprises (e.g. essentially) ortho-xylene, meta-xylene and ethylbenzene. According to one or more embodiments, the para-xylene extraction raffinate comprises (e.g. essentially) meta-xylene and ethylbenzene.

According to one or more embodiments, the hydrocarbon-based feedstock comprises at least 90% by weight of aromatic molecules having 9 carbon atoms relative to the total weight of said feedstock. According to one or more embodiments, the hydrocarbon-based feedstock comprises methylethylbenzenes and optionally trimethylbenzenes, preferably little or no trim ethylbenzenes.

According to one or more embodiments, the hydrocarbon-based feedstock comprises at least 90% by weight of aromatic molecules having 10 carbon atoms relative to the total weight of the hydrocarbon-based feedstock. According to one or more embodiments, the hydrocarbon-based feedstock 2-comprises tetramethylbenzenes and/or dimethylethylbenzenes and/or methylpropylbenzenes, preferably little or no tetramethylbenzenes.

According to one or more embodiments, the hydrocarbon-based feedstock comprises less than 1000 ppm by weight, preferably less than 700 ppm by weight, more preferentially less than 500 ppm by weight, even more preferably less than 300 ppm by weight, of water relative to the total weight of the feedstock.

Integration into an Aromatic Complex

According to one or more embodiments, the hydrogenolysis process is integrated into a process for producing xylenes using an aromatic complex. According to one or more embodiments, the aromatic complex is fed with hydrocarbon-based cuts containing predominantly molecules, the carbon number of which extends from 6 to 10.

According to one or more embodiments, the following configurations of the hydrogenolysis process integrated into an aromatic complex are envisioned:
  the hydrogenolysis process is used to pretreat a hydrocarbon-based feedstock upstream of the aromatic complex. In this case, external streams can directly feed the hydrogenolysis reactor (example 6 to 10 carbon reformate, A9/A10 cut, and the like) and the effluents of the hydrogenolysis reactor are then directed to the aromatic complex.

One or more hydrogenolysis processes are used to treat one or more cuts internal to the aromatic complex. In this case, the hydrogenolysis reactor can be partially or totally fed with one or more streams coming from units (e.g. fractionation/distillation columns, simulated moving bed) of the aromatic complex. The effluents from the hydrogenolysis reactor are then also returned to the aromatic complex.

The combination of the two configurations defined above is also possible and remains within the context of the present invention. In all cases, the effluents are then enriched in aromatics comprising methyl groups which are totally or partially sent to the aromatic complex in order to produce xylenes and optionally benzene. Overall, the integration of the hydrogenolysis process according to the invention into the aromatic complex increases the production of para-xylene.

The invention will now be illustrated by the following examples which are in no way limiting.

EXAMPLES

D—Preparation of the Catalysts

The support chosen for the preparations is a commercial alumina of which the pore volume $Vp=1$ cm$^3$/g and the BET specific surface area=80 m$^2$/g. The support is in the form of multilobe (trilobe or quadrilobe) extrudates (extrusion die diameter 1.6 mm).

Catalyst A (Non-Compliant)

Catalyst A is prepared first of all by dry impregnation of metal salts (carbonates in the case herein), diluted in a solvent that can be vaporized in the heat treatment steps (for example, in the case herein, water or an aqueous solution of ammonia), optionally with a buffer solution to regulate a pH during the impregnation phase which is constant (for example in the present case, ammonium carbonate is used).

The impregnation of nickel (10% by weight), from an ammoniacal nickel carbonate solution, is first of all carried out. Maturation is carried out by leaving the catalyst at ambient conditions overnight. The dry-impregnated catalyst is then dried at 150° C. for 30 min and then calcined at 280° C. for at least 45 minutes in dry air. FX analysis of catalyst A gives a Ni content of 10% by weight, relative to the total weight of the catalyst.

Catalyst B1 (Compliant)

Catalyst B1 is produced from catalyst A by adding a second dry impregnation of Mo (in the form of ammonium heptamolybdate in ammoniacal phase (7% by weight)). Maturation is carried out by leaving the catalyst at ambient conditions overnight. The dry-impregnated catalyst is then dried at 150° C. for 30 min and then calcined at 280° C. for at least 45 minutes in dry air. FX analysis of catalyst B1 gives a Ni content of 9.3% by weight and a Mo content of 7.1% by weight (Mo/Ni=0.47 in molar ratio), relative to the total weight of the catalyst.

Catalyst B2 (Compliant)

Catalyst B2 is produced from catalyst A by adding a second dry impregnation of Mo (in the form of ammonium heptamolybdate in ammoniacal phase). Maturation is carried out by leaving the catalyst at ambient conditions overnight. The dry-impregnated catalyst is then dried at 150° C. for 30 min and then calcined at 280° C. for at least 45 minutes in dry air. FX analysis of catalyst B2 gives a Ni content of 8.1% by weight and a Mo content of 11.9% by weight (Mo/Ni=0.90 in molar ratio), relative to the total weight of the catalyst.

Catalyst B3 (Compliant)

Catalyst B3 is produced from catalyst A by adding a second dry impregnation of Mo (in the form of ammonium heptamolybdate in ammoniacal phase). Maturation is carried out by leaving the catalyst at ambient conditions overnight. The dry-impregnated catalyst is then dried at 150° C. for 30 min and then calcined at 280° C. for at least 45 minutes in dry air. FX analysis of catalyst B3 gives a Ni content of 9.1% by weight and a Mo content of 3.0% by weight (Mo/Ni=0.20 in molar ratio), relative to the total weight of the catalyst.

Catalyst B4 (Non-Compliant)

Catalyst B4 is produced from catalyst A by adding a second dry impregnation of Mo (in the form of ammonium heptamolybdate in ammoniacal phase). Maturation is carried out by leaving the catalyst at ambient conditions overnight. The dry-impregnated catalyst is then dried at 150° C. for 30 min and then calcined at 280° C. for at least 45 minutes in dry air. FX analysis of catalyst B4 gives a Ni content of 9.1% by weight and a Mo content of 1.5% by weight (Mo/Ni=0.10 in molar ratio), relative to the total weight of the catalyst.

E—Catalyst Test Protocol

The operating conditions of the hydrogenolysis step are as follows:

temperature: 390° C.;
pressure: 0.5 MPag;
$H_2$/HC molar ratio: 3 mol/mol;
WWH: 1 to 5 $h^{-1}$ to target a given conversion of methyl-ethylbenzene.

The amount of catalyst charged is 0.016 g.

The feedstock used is a reformate base of the following composition (table 1):

TABLE 1

| Compound | mol % |
|---|---|
| n-propylbenzene | 4.3 |
| 1-methyl-2-ethylbenzene | 10.0 |
| 1-methyl-3-ethylbenzene | 17.6 |
| 1-methyl-4-ethylbenzene | 8.9 |
| 1,2,3-trimethylbenzene | 4.7 |
| 1,2,4-trimethylbenzene | 38.9 |
| 1,3,5-trimethylbenzene | 11.0 |
| Other compounds | 4.6 |
| Total | 100.0 |

The acronym TMB is defined as the sum of the 3 isomers of trimethylbenzene, and MET is defined as the sum of the 3 methyl-ethylbenzenes.

The performance levels of the catalyst are characterized by the following performance indicators:

TMB conversion (mol %)=delta TMB (mol %)/feedstock TMB (mol %);

MET conversion (mol %)=delta MET (mol %)/feedstock MET (mol %);

methyl out/methyl in (mol %)=amount of methyl alkyls on aromatic at the outlet/amount of methyl on aromatic at the inlet;

benzene selectivity corrected for the TMB conversion (mol/mol)=(delta of benzene formed in the products/delta of $A9$+transformed)/((100−TMB conversion)/100);

toluene selectivity corrected for the TMB conversion (mol/mol)=(delta of toluene formed in the products/delta of $A9$+transformed)/(1−TMB conversion);

degree of conservation of aromatic rings=mol % of aromatic carbon at the outlet/mol % of aromatic carbon at the inlet (measured by GC and calculation according to the structure of the molecule).

For each catalyst, a low and a high WWH is scored to target two levels of activity, activity expressed as MET conversion. The catalysts are compared at approximately 60% MET degree of conversion. At this MET conversion, the relative TMB conversions are explored in order to examine the selectivity of the reaction, the objective being to minimize this TMB conversion. The methyl out/methyl in indicator is a base 100 indicator, which depends on the feedstock and on the amount of methyl with respect to a given methyl creation target.

The catalyst performance indicators are as follows (table 2):

TABLE 2

| Catalyst | A | B1 | B2 | B3 | B4 |
|---|---|---|---|---|---|
| Ni (% by weight) | 10 | 9.3 | 8.1 | 9.1 | 9.1 |
| Mo (% by weight) | | 7.1 | 11.9 | 3.0 | 1.5 |
| Mo/Ni (mol/mol) | | 0.47 | 0.90 | 0.20 | 0.10 |
| MET conversion (mol %) | 61.8 | 62.3 | 62.5 | 62.9 | 62.9 |
| TMB conversion (mol %) | 29.7 | 23.0 | 23.4 | 25.6 | 27.4 |
| methyl out/methyl in (mol %) | 100 | 104.0 | 104.4 | 103.3 | 102.9 |
| degree of conversion of aromatic rings (mol/mol) | 98.8 | 99.3 | 98.9 | 99.1 | 99.4 |
| TMB-conversion-corrected benzene selectivity (mol/mol) | 4.3 | 4.5 | 2.7 | 5.1 | 4.8 |
| TMB-conversion-corrected toluene selectivity (mol/mol) | 38.0 | 29.9 | 27.5 | 31.7 | 32.4 |

The Ni vs NiMo comparison according to the invention shows that the NiMo-type catalyst according to the invention is more selective for the relative conversion of TMBs at equal conversion of METs. Indeed, more TMB is preserved and the amount of methyl increases. In addition, a significantly improved selectivity with respect to toluene is observed (i.e. the toluene produced from the reaction is less reactive). In the case of B2, a particularly increased selectivity with respect to benzene is also observed. The degree of preservation of the aromatic rings is also improved (i.e. more limited degree of aromatic hydrogenation).

The increase in the Mo/Ni ratio to 0.90 gives a catalyst which retains an improved selectivity with respect to TMB conversion. However, the catalyst exhibits an increase in the hydrogenating activity on the aromatic rings which limits the increase in the Mo/Ni ratio—this is seen in particular on B2 which has a greater hydrodealkylation. The high Mo/Ni ratio of 0.90 also exhibits improved selectivity with respect to the successive reactions.

The decrease in the Mo/Ni ratio to 0.20 or even 0.10 shows that selectivity of the catalyst with respect to TMB conversion is lost.

To summarize, the NiMo-type catalyst according to the invention is particularly suitable for the conservation of TMBs and for limiting aromatic cycle loss. The NiMo catalyst according to the invention also makes it possible to limit the successive demethylation reactions.

In the present specification, the term "comprise" is synonymous with (signifies the same thing as) "include" and "contain", and is inclusive or open, and does not exclude other elements which are not stated. It is understood that the term "comprise" includes the exclusive and closed term "consist". In addition, in the present description, the terms "approximately", "substantially", "more or less", "essentially", "solely" and "about" are synonymous with (mean the same thing as) margin lower and/or greater by 10%, preferably by 5%, very preferably by 1%, of the given value. For example, a composition comprising essentially or only a compound A corresponds to a composition comprising at least 90%, preferably at least 95%, very preferably at least 99%, of compound A. For example, a duration of substantially 100 min corresponds to a duration of between 90 and 110 min, preferably between 95 and 105 min, very preferably between 99 and 101 minutes

The invention claimed is:

1. A hydrogenolysis process wherein a hydrocarbon-based feedstock comprising aromatic compounds having at least 8 carbon atoms is treated by means of an introduction of hydrogen and in the presence of a catalyst, to convert C2+ alkyl chains of said aromatic compounds into methyl groups and to produce a hydrogenolysis effluent enriched in methyl-substituted aromatic compounds, wherein the hydrogenolysis process is carried out with the following operating conditions:
temperature of between 300° C. and 550° C.;
pressure of between 0.1 and 3 MPa;
$H_2$/HC molar ratio of between 1 and 10;
WWH of between 0.1 and 50 $h^{-1}$, and wherein the catalyst comprises a support comprising at least one refractory oxide, and an active phase comprising nickel and molybdenum, wherein:
the nickel content is between 0.1 and 25% by weight relative to the total weight of the catalyst;
the molybdenum content is between 0.1 and 20% by weight relative to the total weight of the catalyst; and
the catalyst comprises a molar ratio of molybdenum to nickel (Mo/Ni) of between 0.2 and 0.9.

2. The hydrogenolysis process as claimed in claim 1, wherein:
the nickel content is between 0.2 and 15% by weight relative to the total weight of the catalyst;
the molybdenum content is between 0.2 and 18% by weight relative to the total weight of the catalyst; and
the catalyst comprises a molar ratio of molybdenum to nickel of between 0.5 and 0.9.

3. The hydrogenolysis process as claimed in claim 1, wherein:
the nickel content is between 0.5 and 10% by weight relative to the total weight of the catalyst;
the molybdenum content is between 0.4 and 15% by weight relative to the total weight of the catalyst; and
the catalyst comprises a molar ratio of molybdenum to nickel of between 0.4 and 0.9.

4. The hydrogenolysis process as claimed in claim 1, in which the specific surface area (BET) of the refractory oxide is between 1 $m^2$/g and 250 $m^2$/g.

5. The hydrogenolysis process as claimed in claim 1, wherein the pore volume (Vp) of the refractory oxide is between 0.1 and 2 $cm^3$/g.

* * * * *